United States Patent
Tsang et al.

(10) Patent No.: US 7,253,319 B2
(45) Date of Patent: Aug. 7, 2007

(54) DISUBSTITUTED CHALCONE OXIMES HAVING RARγ RETINOID RECEPTOR ANTAGONIST ACTIVITY

(75) Inventors: Kwok Yin Tsang, Irvine, CA (US); Santosh Sinha, Irvine, CA (US); Xiaoxia Liu, Tustin, CA (US); Smita Bhat, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 373 days.

(21) Appl. No.: 11/021,471

(22) Filed: Dec. 23, 2004

(65) Prior Publication Data

US 2005/0165095 A1    Jul. 28, 2005

Related U.S. Application Data

(60) Provisional application No. 60/532,835, filed on Dec. 26, 2003.

(51) Int. Cl.
*C07C 249/00* (2006.01)
*C07D 211/08* (2006.01)
*C07D 335/04* (2006.01)

(52) U.S. Cl. .............. 564/265; 546/192; 546/26; 549/23; 564/253

(58) Field of Classification Search ........... 564/265, 564/253; 546/26, 112, 152, 184, 192, 195, 546/196; 549/13, 23
See application file for complete search history.

(56) References Cited

U.S. PATENT DOCUMENTS

| | | | |
|---|---|---|---|
| 5,455,265 A | 10/1995 | Chandraratna | |
| 5,599,967 A | 2/1997 | Vuligonda et al. | |
| 5,605,915 A | 2/1997 | Vuligonda et al. | |
| 5,723,666 A | 3/1998 | Vuligonda et al. | |
| 5,739,338 A | 4/1998 | Beard et al. | |
| 5,760,276 A | 6/1998 | Beard et al. | |
| 5,877,207 A | 3/1999 | Klein et al. | |
| 5,952,345 A * | 9/1999 | Klein et al. | 514/311 |
| 5,958,954 A | 9/1999 | Klein et al. | |
| 6,225,494 B1 | 5/2001 | Song et al. | |
| 6,455,701 B1 | 9/2002 | Song et al. | |
| 6,469,208 B1 | 10/2002 | Villax et al. | |
| 2002/0082265 A1* | 6/2002 | Lapierre et al. | 514/255.06 |

FOREIGN PATENT DOCUMENTS

| | | |
|---|---|---|
| EP | 024 982 | 3/1981 |
| WO | WO 93/11755 | 6/1993 |
| WO | WO 94/14777 | 7/1994 |
| WO | WO 02/28810 A2 | 4/2002 |

OTHER PUBLICATIONS

Mangelsdorf et al. (1994) The Retinoid Receptors In: The Retinoids, edited by Sporn et al. p. 319-349. Raven Press. Ltd., New York.
Dawson and William H. Okamura, Chemistry and Biology of Synthetic Retinoids, Published by CRC Press Inc., 1990, pp. 324-356.
Yoshimura et al. J. Med. Chem. 38: 3163-3173 (1995).
Kaneko et al. Med. Chem Res. 1: 220-225 (1991).
Apfel et al. *Proc. Natl. Acad. Sci.* USA 89: 7129-7133 Augusty 1992 Cell Biology.
Eckhardt et al. Toxicology Letters 70:229-308 (1994).
Keidel et al. Molecular and Cellular Biology 14: 287-298 (1994).
Eyrolles et al. J. Med. Chem. 37: 1508-1517 (1994).
Feigner P. L. and Holm M. (1989) Focus, 112.
Heyman et al. Cell 68, 397-406, (1992).
Allegretto et al. J. Bio Chem. 268,26625-26633.
Teng et al. J. Chem. 40, 2445-2452, (1997).
Cheng et al. Biochemical Pharmacology vol. 22 pp. 3099-3108.

* cited by examiner

*Primary Examiner*—Karl Puttlitz
(74) *Attorney, Agent, or Firm*—Hamilton, Brook, Smith & Reynolds, P.C.

(57) ABSTRACT

Compounds of the formula

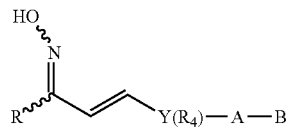

where the variables have the values described in the specification are antagonists of RAR$_\gamma$ retinoid receptors.

18 Claims, No Drawings

DISUBSTITUTED CHALCONE OXIMES HAVING RARγ RETINOID RECEPTOR ANTAGONIST ACTIVITY

This Application claims the benefit of Provisional Application 60/532,835, filed Dec. 26, 2003.

BACKGROUND OF THE INVENTION

1. Field of the Invention

The present invention is directed to compounds having $RAR_\gamma$ retinoid receptor antagonist activity. More specifically, the present invention is directed to disubstituted chalcone oximes that have $RAR_\gamma$ retinoid receptor antagonist activity.

2. Background Art

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. The prior art has developed a large number of chemical compounds which have retinoid-like biological activity, and voluminous patent and chemical literature exists describing such compounds.

Unfortunately, compounds having retinoid-like activity (retinoids) also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types, is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356.

Compounds have also been developed in the art which bind to RAR receptors without triggering the response or responses that are triggered by agonists of the same receptors. The compounds or agents which bind to RAR receptors without triggering a "retinoid" response are thus capable of blocking (to lesser or greater extent) the activity of RAR agonists in biological assays and systems. Such compounds are described, for example, in U.S. Pat. Nos. 5,877,207; 5,952,345 and 5,958,954. As further literature in this field published PCT Application WO 94/14777 is noted that describes certain heterocyclic carboxylic acid derivatives which bind to RAR retinoid receptors and are said in the application to be useful for treatment of certain diseases or conditions, such as acne, psoriasis, rheumatoid arthritis and viral infections. A similar disclosure is made in the article by Yoshimura et al. *J. Med. Chem.* 38: 3163–3173 (1995). Kaneko et al. *Med. Chem Res.* 1:220–225 (1991); Apfel et al. *Proc. Natl. Acad. Sci. USA* 89: 7129–7133 Augusty 1992 *Cell Biology*; Eckhardt et al. *Toxicology Letters* 70:299–308 (1994); Keidel et al. *Molecular and Cellular Biology* 14:287–298 (1994); and Eyrolles et al. *J. Med. Chem.* 37: 1508–1517 (1994) describe compounds which have antagonist like activity at one or more of the RAR retinoid subtypes.

"Chalcone moiety" or "chalcone linker" and "chalcone oxime linker" are terms for describing in this application moieties that have the structure shown below

CHALCONE LINKER      CHALCONE OXIME LINKER and which in the present invention covalently link two aromatic or heteroaromatic moieties. In the formula the stars indicate the carbons to which the aromatic rings are attached, respectively.

The following references disclose retinoid compounds which are disubstituted "chalcone" compounds: U.S. Pat. Nos. 6,455,701; 6,469,028; 6,225,494; 5,723,666; 5,739,338 and 5,760,276.

PCT Publication WO 02/28810 A2 discloses compounds useful for treating emphysema and associated pulmonary diseases and the general formulas provided in this disclosure include chalcone oxime compounds.

U.S. Pat. Nos. 5,723,666; 5,599,967; and 5,605,915 disclose retinoid compounds which include an oxime moiety.

In addition to undesirable side-effects of therapy with retinoid compounds, there occurs occasionally a serious medical condition caused by vitamin A or vitamin A precursor overdose, resulting either from the excessive intake of vitamin supplements or the ingestion of liver of certain fish and animals that contain high levels of the vitamin. The chronic or acute toxicities observed with hypervitaminosis A syndrome include headache, skin peeling, bone toxicity, dyslipidemias, etc. In recent years, it has become apparent that the toxicities observed with vitamin A analogs, i.e., retinoids, essentially recapitulate those of hypervitaminosis A syndrome, suggesting a common biological cause, i.e., RAR activation. Although some retinoid antagonists are known in the art, the above-noted retinoid-caused toxicities are presently treated mainly by supportive measures and by abstaining from further exposure to the causative agent, whether it is liver, vitamin supplements, or retinoids. While some of the toxicities resolve with time, others (e.g., premature epiphyseal plate closure) are permanent.

Generally speaking, specific antidotes are the best treatment for poisoning by pharmacological agents, but only about two dozen chemicals or classes of chemicals out of thousands in existence have specific known antidotes. Specific antidotes would clearly be of value in the treatment of hypervitaminosis A and retinoid toxicity. Indeed, as increasingly potent retinoids are used clinically, a specific antidote for retinoid poisoning could be life saving. Moreover, because many known retinoids are selective to one more retinoid receptor subtypes, and because of the various biological pathways activated by the different retinoid receptor subtypes, and still further because of the varying distribution of the retinoid subtypes in the mammalian organs, compounds which are antagonists to $RAR_\gamma$ receptors, and particularly compounds which are specific or selective antagonists of $RAR_\gamma$ receptors are pharmacologically desirable. The present invention provides such compounds.

SUMMARY OF THE INVENTION

The present invention relates to compounds of Formula 1

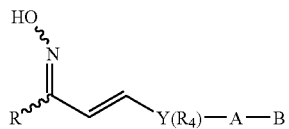

Formula 1 wherein R is selected from the groups consisting of the radicals defined by formulas (a) through (d)

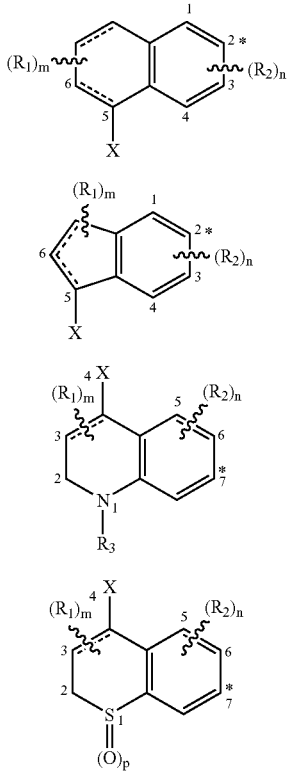

where the dashed line in a ring represents a bond, or absence of a bond with the proviso that one and only one dashed line in the ring represents a bond;

a * denotes a ring carbon to which the chalcone oxime group is attached;

X is $(R_5)_r$-substituted alkenyl of 1–6 carbons and 1 or 2 double bonds, $(R_5)_r$-substituted alkynyl of 1–6 carbons and 1 or 2 triple bonds, $(R_5)_r$-phenyl, $(R_5)_r$-naphthyl, $(R_5)_r$-heteroaryl where the heteroaryl group has 1 to 3 heteroatoms selected from the group consisting of O, S and N;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_4$ groups;

m is an integer having the values 0 to 5;
n is an integer having the values 0 to 3;
p is an integer having the values 0 to 2;
r is an integer having the values 0 to 5;
$R_1$ is independently alkyl of 1 to 6 carbons, F, Cl, Br or I;
$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
$R_3$ is H or alkyl of 1 to 10 carbons;
$R_4$ is independently halogen, alkyl of 1 to 10 carbons, fluoro substituted alkyl of 1 to 6 carbons, alkoxy of 1 to 10 carbons, or alkylthio of 1 to 10 carbons;
$R_5$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;
A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;
B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

The present invention also relates to pharmaceutical compositions incorporating the compounds of Formula 1 and to methods of treatment of mammals in need of such treatment, with a retinoid antagonist, and particularly to methods of preventing, treating or ameliorating retinoid poisoning, overdose by a retinoid, or in conjunction with a retinoid where the activation of $RAR_\gamma$ receptor by the retinoid is not desired, or is to be minimized.

DETAILED DESCRIPTION OF THE INVENTION

General Embodiments and Synthetic Methodology

Definitions

The term alkyl refers to and covers any and all groups which are known as normal alkyl and branched-chain alkyl.

A pharmaceutically acceptable salt may be prepared for any compound in this invention having a functionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include at least one olephinic double bond about which trans and cis (E and Z) stereoisomerism can exist. The compounds of the present invention have the specific orientations of substituents relative to the double bond or double bonds, as is indicated in the name of the respective compound, and/or by specific showing in the structural formula of the orientation of the substituents relative to the double bond or double bonds.

The compounds of the invention also include an oxime function that is attached to the adjacent carbon by a double bond about which syn and anti stereoisomerism exists. The scope of the invention is intended to cover oximes in both syn and anti configuration. However, the specific examples have the specific configuration that is indicated in their respective chemical names and/or is shown by the respective structural formulas.

The compounds of the present invention may also contain one or more chiral centers and therefore may exist in enantiomeric and diastereomeric forms. With regard to the chiral centers in the compounds, the scope of the invention is intended to cover all possible orientations of the substituents, thus including pure enantiomers (optical isomers), diastereomers, mixtures of diastereomers and racemic mixtures of enantiomers.

Generally speaking the compounds of the invention can be obtained by the synthetic route shown in Reaction Scheme 1.

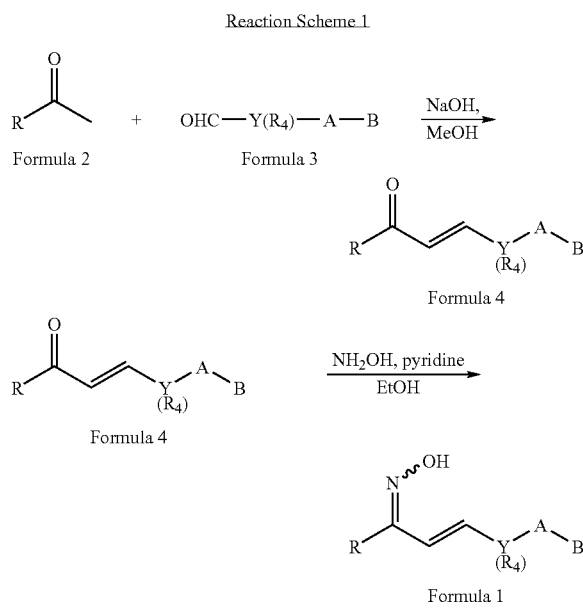

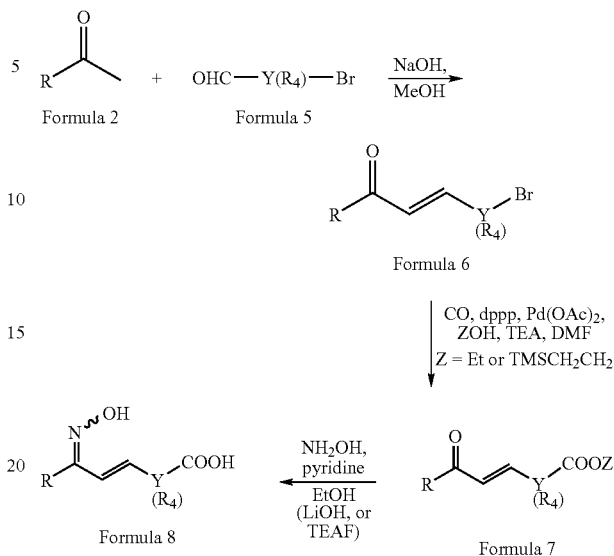

The starting compound in Reaction Scheme 1 is a methyl ketone of Formula 2 where the variable R is defined as in connection with Formula 1. The methyl ketone of Formula 2 is reacted with an aldehyde of Formula 3 in the presence of strong base, such as sodium hydroxide, in a suitable polar solvent, such as methanol. The result of this aldol condensation reaction is a compound of Formula 4 where the R group and the substituted aromatic or heteroaromatic Y group are covalently linked with the chalcone moiety CO=CH=CH. The compound of Formula 4 is then reacted in a suitable polar solvent, such as ethyl alcohol, with hydroxylamine in the presence of pyridine to provide the oxime compounds of the invention of Formula 1. Usually oximes of both syn and anti (or cis and trans) configuration are formed in the last reaction, but not necessarily in equal amounts. In most instances the isomeric oximes can be separated from each other by crystallization and/or chromatography.

In a variation of the synthetic route shown in Reaction Scheme 1 the A-B group of Formula 3 is replaced with a bromo group as shown in Formula 5. In this variation, after the aldol condesation reaction the product (Formula 6) is converted to a compound of Formula 7 by reaction with carbon monoxide in the presence of 1,3-bis(diphenylphosphino)-propane (dppp) and palladium acetate in dimethylformamide (DMF), triethylamine (TEA) and ethanol, or 2-(trimethylsilyl)ethanol. The chalcone compound of Formula 7 is then converted to the oxime of Formula 8 by reaction with hydroxylamine in the presence of pyridine or other base. The compounds of Formula 8 are within the scope of the invention and within the scope of Formula 1.

The methyl ketones of Formula 2 are usually available in accordance with the chemical patent and/or scientific literature, or can be obtained by such modifications of known synthetic methods which are readily within the skill of the practicing organic chemist. Reaction Schemes 2 and 3 disclose general synthetic routes that provide the methyl ketone of Formula 2.

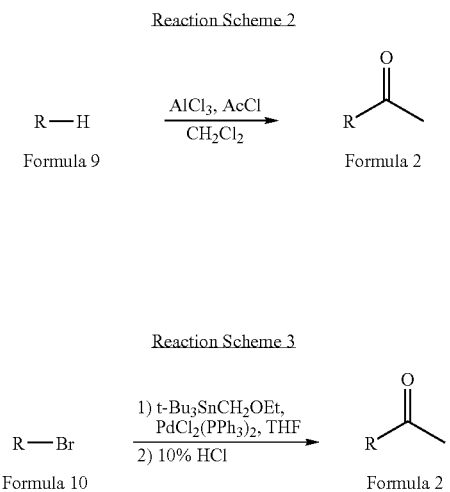

In accordance with Reaction Scheme 2 a compound of Formula 9 is subjected to a Friedel Crafts reaction with acetyl chloride in a suitable aprotic solvent, such as methylene chloride, to provide the methyl ketone of Formula 2. In accordance with Reaction Scheme 3 a bromo compound of Formula 10 is reacted in a suitable aprotic solvent, such as tetrahydrofuran (THF), under a protective blanket of an inert gas, such as argon, with tributyl(1-ethoxyvinyl)tin in the presence of a palladium catalyst ($PdCl_2(PPh_3)_2$), and thereafter with acid to provide the methyl ketone of Formula 2. The starting materials in these reactions, namely the compounds of Formulas 9 and 10 are available in accordance with the chemical patent and/or scientific literature, or can be obtained by such modifications of known synthetic methods which are readily within the skill of the practicing organic chemist. Examples for the compounds of Formulas 2, 9 and 10 are provided in connection with the specific examples disclosed below together, where applicable, with the presently preferred method for synthesizing these compounds.

The aromatic or heteroaromatic aldehyde reagents of Formulas 3 and 5 in Reaction Scheme 1 where the variables Y, $R_4$, A and B are defined as in connection with Formula 1 are also available in accordance with the chemical patent and/or scientific literature, or can be obtained by such modifications of known synthetic methods which are readily within the skill of the practicing organic chemist.

Examples for the aromatic or heteroaromatic aldehyde reagents of Formulas 3 and 5 usable in Reaction Scheme 1 are methyl-4-formylbenzoate, methyl 4-formyl-2-fluoro-benzoate, 4-bromo-2-fluoro-benzaladehyde, 4-bromobenzaldehyde, methyl-3-formylbenzoate, methyl 3-formyl-2-fluoro-benzoate, 3-bromo-2-fluoro-benzaladehyde, 3-bromobenzaldehyde, methyl-5-formyl-naphthoate, methyl-6-formyl-naphthoate, methyl-5-formyl-thiophene-2-carboxylate, methyl-5-formyl-thiophene-3-carboxylate, methyl-5-formyl-furan-2-carboxylate, methyl-5-formyl-furan-3-carboxylate, methyl-6-formyl-pyridine-2-carboxylate, methyl-6-formyl-pyridine-3-carboxylate, 1-bromo-5-formyl-naphthalene, 1-bromo-4-formyl-naphthalene, 2-bromo-5-formyl-thiophene, 3-bromo-5-formyl-thiophene, 2-bromo-5-formyl-furan, 3-bromo-5-formyl-furan, 3-bromo-6-formyl-pyridine and 2-bromo-6-formyl-pyridine.

Biological Activity, Modes of Administration

The compounds of the invention were tested in certain assays for activity as agonists of RAR and RXR retinoid receptors, and also for their ability to bind to said receptors without activating them, namely for their activity as antagonists of RAR and RXR receptors.

Specifically, one assay in which the compounds were tested is a chimeric receptor transactivation assay which tests for agonist-like activity in the $RAR_\alpha$, $RAR_\beta$ and $RAR_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The other functional assay running in the presence of 1 nM all-trans retinoic acid, namely PGA-RAR antagonist assay (utilizing glucocorticoid-retinoid chimeric receptors), is a modified chimeric receptor transactivation assay which tests the compounds for their antagonist-like activity in the $RAR_\alpha$, $RAR_\beta$ and $RAR_\gamma$ receptor subtypes. The results from this assay are normally expressed in $IC_{50}$ numbers (See Teng et al. J. Med. Chem. 40, 2445–2452, (1997) incorporated herein by reference.)

The results of the ligand binding assay are expressed in $K_i$ numbers. (See Cheng et al. Biochemical Pharmacology Vol. 22 pp 3099–3108, expressly incorporated herein by reference.)

Percentage inhibition in an antagonist assay is expressed as a percentage of the maximum inhibition of the transaction activity induced by 1 nM all-trans retinoic acid.

Table 1 discloses the activity of certain exemplary compounds of the invention in the above-described chimeric RAR receptor transactivation and binding assays. In the holoreceptor transactivation assay the compounds were essentially inactive in activating $RXR_\alpha$, $RXR_\beta$ and $RXR_\gamma$ receptors and these data are not shown.

TABLE 1

| Compound | RAR Binding | | | RAR EC50 (nM) (% Efficiency) | | | RAR IC50 (nM) (% Inhibition) | | |
|---|---|---|---|---|---|---|---|---|---|
| | α | β | γ | α | β | γ | α | β | γ |
| 7a | 3k | 5k | 3 | >10k | >10k | >10k | >1k | >1k | 0.6 (95%) |
| 7b | 5.2k | 1.9k | 29 | >10k | >10k | >10k | >1k | >1k | 25 (88%) |
| 7c | 2.9k | 1.3k | 6 | >10k | >10k | >10k | >50k | >100k | 2 (108%) |
| 9a | 13k | 15k | 11 | >10k | >10k | >10k | >1k | >1k | 5 (90%) |

TABLE 1-continued

| Compound | RAR Binding | | | RAR EC50 (nM) (% Efficiency) | | | RAR IC50 (nM) (% Inhibition) | | |
|---|---|---|---|---|---|---|---|---|---|
| | α | β | γ | α | β | γ | α | β | γ |
| 9b | 13k | 10k | 133 | >10k | >10k | >10k | >1k | >1k | 13 (78%) |
| 16a | 9k | 10k | 25 | >10k | >10k | >10k | >1k | >1k | 27 (78%) |
| 16b | 7k | 10k | 145 | >10k | >10k | >10k | >1k | >1k | 67 (54%) |
| 18a | 12k | 10k | 70 | >10k | >10k | >10k | >1k | >1k | 52 (70%) |

TABLE 1-continued

| Compound | RAR Binding | | | RAR EC50 (nM) (% Efficiency) | | | RAR IC50 (nM) (% Inhibition) | | |
|---|---|---|---|---|---|---|---|---|---|
| | α | β | γ | α | β | γ | α | β | γ |
| 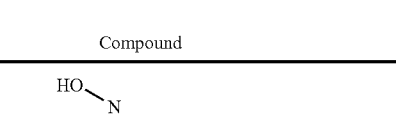 18b | 23k | 10k | 717 | >10k | >10k | >10k | >1k | >1k | 226 (58%) |

As it can be seen from the test results shown in Table 1, the therein indicated exemplary compounds of the invention are antagonists of the $RAR_\gamma$ receptor subtypes, but have no or much less affinity to $RAR_\alpha$ or to $RAR_\beta$ receptor subtypes. Due to this property, the compounds of the invention can be used to selectively or specifically block the activity of $RAR_\gamma$ agonists in biological assays. Thus, in mammals, including humans, the compounds of the invention can be coadministered with RAR agonists and, by means of their pharmacological specificity, selectivity or site-specific delivery, preferentially prevent or diminish the undesired effects of the agonist on $RAR_\gamma$ receptors.

For example, the compounds of the invention can be used to treat Vitamin A overdose, acute or chronic, resulting either from the excessive intake of vitamin A supplements or from the ingestion of liver of certain fish and animals that contain high level of Vitamin A. Still further, the compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the compounds of the present invention block $RAR_\gamma$ activation, they are suitable for treating the foregoing toxicities.

The compounds of the invention are able to substantially prevent skin irritation induced by $RAR_\gamma$ agonist retinoids, when the compound of the invention is topically coadministered to the skin. Similarly, compounds of the invention can be administered topically to the skin, to block skin irritation, in patients or animals who are administered $RAR_\gamma$ agonist compounds systemically. The compounds of the invention can accelerate recovery from pre-existing retinoid toxicity, may contribute to blocking hypertriglyceridemia caused by co-administered retinoids, and may contribute to blocking bone toxicity induced by an RAR agonist (retinoid).

Generally speaking, for therapeutic applications in mammals in accordance with the present invention, the antagonist compounds can be administered enterally or topically as an antidote to vitamin A, vitamin A precursors, or antidote to retinoid toxicity resulting from overdose or prolonged exposure, after intake of the causative factor (vitamin A precursor or other retinoid) has been discontinued. Alternatively, the antagonist compounds are coadministered with retinoid drugs in accordance with the invention, in situations where the retinoid provides a therapeutic benefit, and where the coadministered antagonist alleviates or eliminates one or more undesired side effects of the retinoid. For this type of application the antagonist may be administered in a site-specific manner, for example as a topically applied cream or lotion while the coadministered retinoid may be given enterally.

For therapeutic applications in accordance with the present invention the antagonist compounds are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For example, preparation of topical formulations are well described in *Remington's Pharmaceutical Science*, Edition 17, Mack Publishing Company, Easton, Pa. For topical application, the antagonist compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the antagonist compound will be prepared as a solution or suspension capable of being administered by injection. In certain cases, it may be useful to formulate the antagonist compounds by injection. In certain cases, it may be useful to formulate the antagonist compounds in suppository form or as extended release formulation for deposit under the skin or intramuscular injection.

The antagonist compounds will be administered in a therapeutically effective dose in accordance with the invention. A therapeutic concentration will be that concentration which effects reduction of the particular condition (such as toxicity due to retinoid or vitamin A exposure, or side effect of retinoid drug) or retards its expansion. It should be understood that when coadministering the antagonist compounds to block retinoid-induced toxicity or side effects in accordance with the invention, the antagonist compounds are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of antagonist compound per mililiter of formulation will constitute a therapeutically effective concentration for topical application. If administered systemically, an amount between 0.01 and 5 mg per kg per day of body weight would be expected to effect a therapeutic result.

Specific Embodiments of the Compounds of the Invention

Referring now to Formula 1, in the preferred compounds of the invention the variable R represents a substituted 7,8-dihydronaphtalen-2-yl group, or a substituted ind-5,6-en-2-yl group, a substituted thiochromen-7-yl group, or a substituted 1,2-dihydroquinolin-7-yl group.

The variable $R_1$ in the preferred compounds of the invention is alkyl of 1 to 6 carbons, more preferably alkyl of 1 to 3 carbons, and most preferably methyl. The variable m is preferably two (2) and in the most preferred compounds of the invention there are two (geminal) methyl groups in the 8 position of the 7,8-dihydronaphthalene and in the 7 position of the ind-5,6-ene nucleus.

In the presently preferred compounds of the invention the aromatic portion of the moiety designated R is either unsubstitited with an $R_2$ group (n is zero) or substituted with one or two $R_2$ groups which are preferably alkyl of 1 to 6 carbons, more preferably alkyl of 1 to 3 carbons. Presently most preferably the aromatic portion of the condensed ring system is not substituted with an $R_2$ group (n is zero.)

In the preferred compounds of the invention the group designated X is a phenyl group. Presently, the phenyl group is preferably substituted with one $R_5$ group (r is one) and the $R_5$ group is presently preferred as alkyl of 1 to 6 carbons, more preferably alkyl of 1 to 3 carbons, and presently most preferably methyl.

The aromatic or heteroaromatic radical represented by Y is preferably phenyl, pyridyl, thienyl or furyl. Even more preferably Y is phenyl, and more preferably the phenyl group is substituted by the chalcone oxime linker and the A-B group in the 1,4 (para) position. When Y is pyridyl, it is preferably substituted by the chalcone oxime linker and the A-B group in the 2,5 position. The thienyl or furyl groups are preferably substituted by the chalcone oxime linker and the A-B group in the 2,4 or 2,5 positions.

In the preferred compounds of the invention either there is no $R_4$ substituent or $R_4$ represents halogen, and even more preferably a fluoro group.

The A-B group preferably represents $(CH_2)_q$—COOH, $(CH_2)_q$—COOR$_8$, or $(CH_2)_q$—CONR$_9$R$_{10}$. More preferably q is zero (0) and B is COOH, the cation of a pharmaceutically acceptable salt, or $R_8$ is alkyl of 1 to 3 carbons, or methoxymethyl. In the most preferred compounds of the invention $R_8$ is H or the cation of a pharmaceutically acceptable salt.

The structures of the presently most preferred compounds of the invention are shown in Table 1, and the experimental procedures for their syntheses are described below.

Synthesis of Dihydronaphthalene Exemplary Compounds of the Invention

Reaction Scheme 4

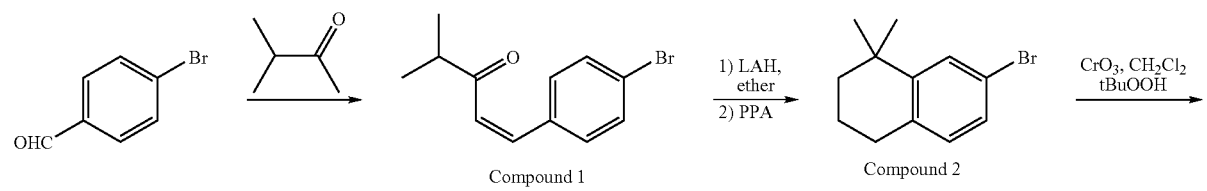

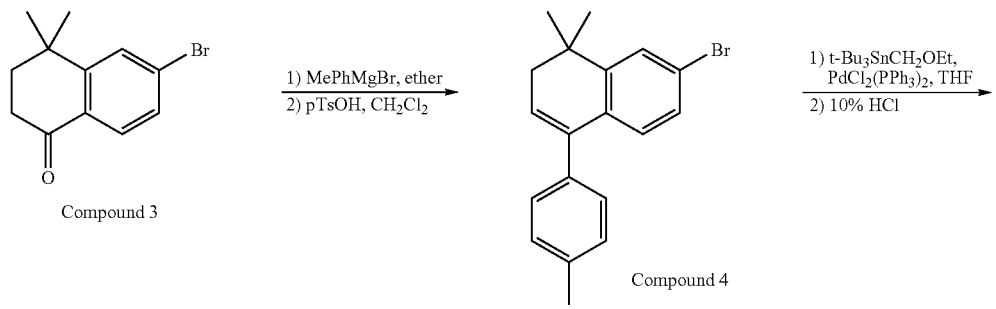

-continued

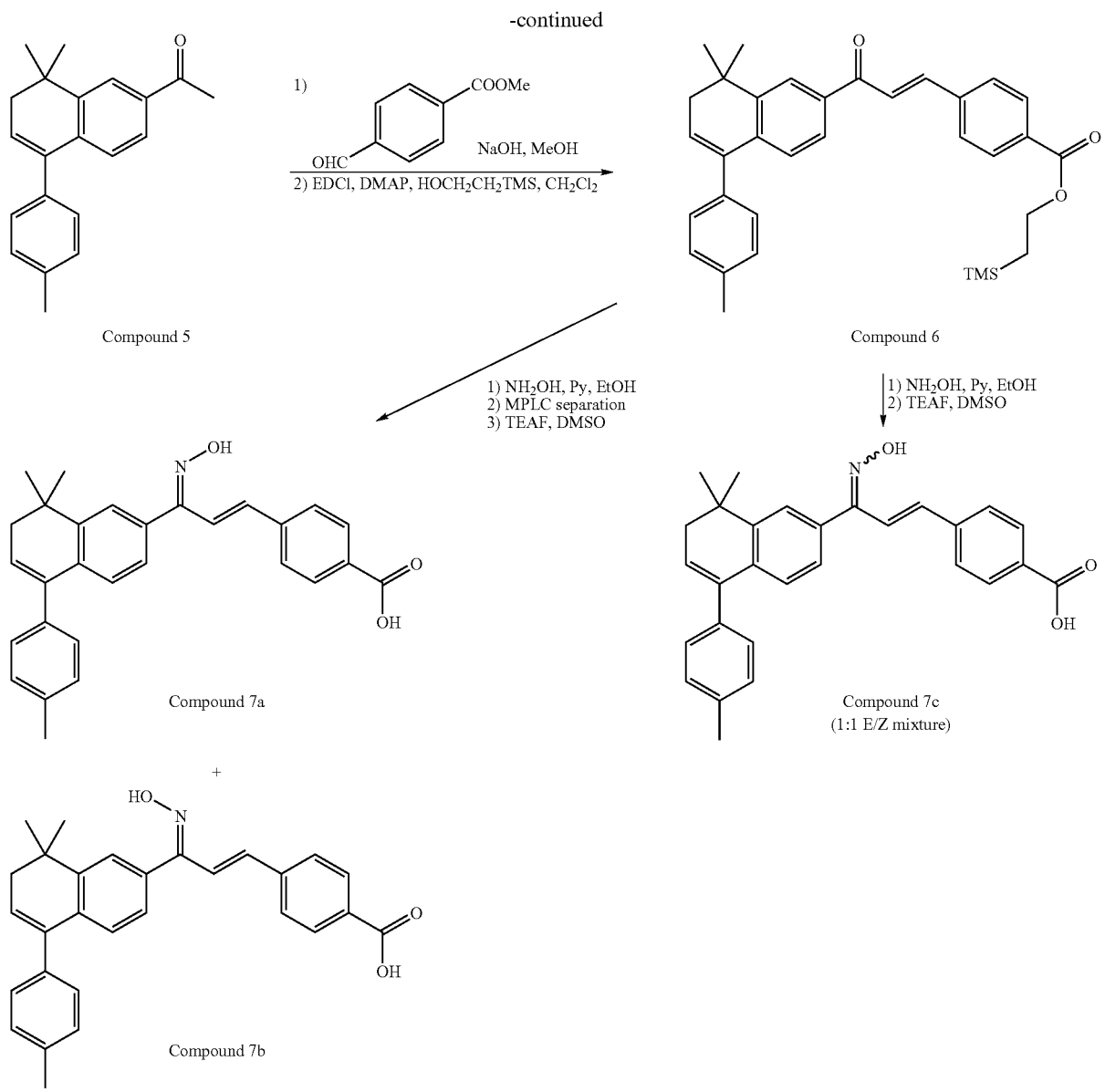

1-(4-Bromo-phenyl)-4-methyl-pent-1-en-3-one (Compound 1)

4-Bromo-benzaldehyde (available from Aldrich, 10.0 g, 54.3 mmol) was added to a solution of 3-methyl-butan-2-one (available from Aldrich, 4.7 g, 54.7 mmol) in 10 mL of 10% NaOH$_{(aq)}$ and 20 mL of ethanol. After stirring at room temperature for 3 h, the reaction mixture was diluted with water (50 mL) and extracted with diethyl ether (3×20 mL). The organic layer was then washed with brine (1×5 mL), dried (MgSO$_4$) and concentrated at reduced pressure. Purification by flash chromatography (95:5 hexane/ethyl acetate) yielded the title compound (7.98 g, 58% yield) as a light yellow oil:

$^1$H NMR (CDCl$_3$, 300 MHz) δ 7.54 (d, J=16.2 Hz, 1H), 7.53 (d, J=8.7 Hz, 2H), 7.42 (d, J=8.7 Hz, 2H), 6.80 (d, J=16.2 Hz, 2H), 2.93–2.87 (m, 1H), 1.18 (d, J=6.9 Hz, 6H).

7-Bromo-1,1-dimethyl-1,2,3,4-tetrahydro-naphthalene (Compound 2)

To a solution of 1-(4-bromo-phenyl)-4-methyl-pent-1-en-3-one (Compound 2, 7.98 g, 31.7 mmol) in 20 mL diethyl ether at 0° C. was slowly added lithium aluminum hydride (LAH) (1.20 g, 38.0 mmol). After stirring and warming to room temperature for 1 h, the reaction was quenched by 2 mL of saturated ammonium chloride solution at 0° C. with an ice bath and dried over anhydrous MgSO$_4$. Solids were removed by filtration and the filtrate was concentrated at reduced pressure to obtain a crude colorless oil. 5 g of polyphosphoric acid (PPA) was then added to the crude oil and the mixture was heated at 120° C. for 15 min. After cooling to room temperature, the mixture was taken up in water (100 mL), extracted with diethyl ether (3×15 mL), washed with brine (1×15 mL), dried (MgSO$_4$) and concentrated at reduced pressure. Purification by flash chromatography (hexane) yielded the title compound (6.70 g, 89% yield) as a light yellow oil:

$^1$H NMR (CDCl$_3$, 300 MHz) δ 7.35 (d, J=2.1 Hz, 1H), 7.09 (dd, J=1.8, 8.1 Hz, 1H), 6.83 (d, J=8.4 Hz, 1H), 2.60 (t, J=6 Hz, 2H), 1.75–1.59 (m, 2H), 1.56–1.47 (m, 2H), 1.19 (s, 6H).

6-Bromo-4,4-dimethyl-3,4-dihydro-2H-naphthalen-1-one (Compound 3)

To a solution of 7-bromo-1,1-dimethyl-1,2,3,4-tetrahydro-naphthalene (Compound 2, 1.1 g, 4.62 mmol) in 10 mL of dichloromethane was added chromium (VI) oxide (72 mg, 0.46 mmol) and 5 mL of tert-butyl hydroperoxide solution (TBHP). After stirring at room temperature for 8 h, the mixture was diluted with water (20 mL), extracted with diethyl ether (3×10 mL), washed with brine (1×10 mL), dried (MgSO$_4$) and concentrated at reduced pressure. Purification by flash chromatography (90:10 hexane/ethyl acetate) yielded the title compound (920 mg, 79% yield) as a white solid:

$^1$H NMR (CDCl$_3$, 300 MHz) δ 7.87 (d, J=8.1 Hz, 1H), 7.54 (d, J=2.1 Hz, 1H), 7.42 (dd, J=2.1, 8.1 Hz, 1H), 2.70 (dd, J=6.3, 7.5 Hz, 2H), 2.01 (dd, J=6.3, 7.5 Hz, 2H), 1.38 (s, 6H).

7-Bromo-1,1-dimethyl-4-p-tolyl-1,2-dihydro-naphthalene (Compound 4)

p-Tolyl magnesium bromide (1 M solution in diethyl ether, 4.2 mL, 4.17 mmol) was added slowly to a solution of 6-bromo-4,4-dimethyl-3,4-dihydro-2H-naphthalen-1-one (Compound 3, 350 mg, 1.39 mmol) in 10 mL of diethyl ether at 0° C. After stirring and warming to room temperature for 2 h, the mixture was quenched with water at 0° C., extracted with diethyl ether (3×5 mL), washed with brine (1×5 mL), dried (MgSO$_4$) and concentrated at reduced pressure to give a light yellow oil. The crude oil was then dissolved in 10 mL of dichloromethane and stirred with 100 mg of para-toluenesulfonic acid at room temperature for 2 h. Water (10 mL) was then added and the organic layer was washed with brine (1×5 mL), dried (MgSO$_4$) and concentrated at reduced pressure. Purification by flash chromatography (hexane) gave the title compound (295 mg, 65% yield) as a colorless oil:

$^1$H NMR (CDCl$_3$, 300 MHz) δ 7.49–7.45 (m, 2H), 7.26–7.18 (m, 4H), 6.90 (d, J=8.1 Hz, 1H), 5.97 (t, J=4.8 Hz, 1H), 2.39 (s, 3H), 2.30 (d, J=4.8 Hz, 2H), 1.30 (s, 6H).

1-(8,8-Dimethyl-5-p-tolyl-7,8-dihydro-naphthalen-2-yl)-ethanone (Compound 5)

A solution of 7-bromo-1,1-dimethyl-4-p-tolyl-1,2-dihydro-naphthalene (Compound 4, 295 mg, 0.90 mmol) in 5 ml of THF was first degassed by bubbling with argon for 30 min. Tributyl(1-ethoxyvinyl)tin (650 mg, 1.80 mmol) and PdCl$_2$(PPh$_3$)$_2$ (63 mg, 0.09 mmol) were added. After stirring at 80° C. for 18 h, the mixture was cooled to room temperature and 3 mL of 10% HCl was added. The mixture was then stirred for another 30 min before extraction with ethyl acetate (3×10 mL). The combined organic layer was washed with brine (1×10 mL), dried (MgSO$_4$) and concentrated at reduced pressure. Purification by flash chromatography (80:20 hexane/ethyl acetate) afforded the title compound (248 mg, 95% yield) as a colorless oil:

$^1$H NMR (CDCl$_3$, 300 MHz) δ 7.97 (d, J=1.8 Hz, 1H), 7.66 (dd, J=1.8, 8.1 Hz, 1H), 7.21 (s, 4H), 7.11 (d, J=8.1 Hz, 1H), 6.09 (t, J=4.5 Hz, 1H), 2.61 (s, 3H), 2.58–2.37 (m, 5H), 1.37 (s, 6H).

2-Trimethylsilanyl-ethyl 4-[3-(8,8-dimethyl-5-p-tolyl-7,8-dihydro-naphthalen-2-yl)-3-oxo-propenyl]-benzoate (Compound 6)

Methyl 4-formylbenzoate (available from Aldrich, 113 mg, 0.69 mmol) was added to a solution of 1-(8,8-dimethyl-5-p-tolyl-7,8-dihydro-naphthalen-2-yl)-ethanone (Compound 5, 200 mg, 0.69 mmol) in 10 mL of 1 N NaOH and 20 mL of methanol. After stirring at room temperature for 18 h, the reaction mixture was acidified with 1N HCl and extracted with ethyl acetate (3×10 mL). The combined organic layer was washed with brine (1×10 mL), dried (MgSO$_4$) and concentrated at reduced pressure to give a yellow crude solid. This crude solid was then dissolved in 10 mL of dichloromethane and 1 mL of trimethylsilylethanol at 0° C. 1-(3-dimethylaminopropyl)-3-ethylcarbodiimide hydrochloride (EDCI) (265 mg, 1.38 mmol) and 4-dimethylaminopyridine (DMAP) (6 mg, 0.07 mmol) were added. After stirring at room temperature for 18 h, the reaction was quenched with water (10 mL), extracted with dichloromethane (3×10 mL), washed with brine (1×10 mL), dried (MgSO$_4$) and concentrated at reduced pressure. Purification by flash chromatography (90:10 hexane/ethyl acetate) yielded the title compound (155 mg, 43% yield) as a yellow oil:

$^1$H NMR (CDCl$_3$, 300 MHz) δ 8.00–7.93 (m, 3H), 7.75–7.42 (m, 5H), 7.17–7.06 (m, 5H), 6.03 (t, J=4.5 Hz, 1H), 4.37–4.32 (m, 2H), 2.31–2.27 (m, 5H), 1.31 (s, 6H) 1.19–1.16 (m, 2H), 0.00 (s, 9H).

Procedure A E-4-[3-(8,8-Dimethyl-5-p-tolyl-7,8-dihydro-naphthalen-2-yl)-3-hydroxyimino-propenyl]-benzoic acid (Compound 7a) and Z-4-[3-(8,8-dimethyl-5-p-tolyl-7,8-dihydro-naphthalen-2-yl)-3-hydroxyimino-propenyl]-benzoic Acid (Compound 7b)

To a solution of 2-trimethylsilanyl-ethyl 4-[3-(8,8-dimethyl-5-p-tolyl-7,8-dihydro-naphthalen-2-yl)-3-oxo-propenyl]-benzoate (Compound 6, 226 mg, 0.43 mmol) in 5 mL of EtOH was added hydroxylamine hydrochloride (60 mg, 0.86 mmol) and pyridine (71 mg, 0.90 mmol). The reaction mixture was then heated at reflux for 6 h. After cooling to room temperature, the solvent was removed in vacuo and the residue was taken up in water. The aqueous layer was adjusted to pH=4–5 with 1 N HCl and extracted with ethyl acetate (3×10 mL). The organic layers were combined and washed with water (2×10 mL) and brine (1×10 mL), dried (MgSO$_4$) and concentrated at reduced pressure. Separation of the E- and Z-isomers was achieved with the ester intermediates by medium pressure liquid chromatography (MPLC) (80:20 hexane/ethyl acetate). Each ester was then dissolved in 2 mL of dimethylsulfoxide (DMSO) and 2 equivalence of tetraethylammomium fluoride (TEAF) was added. After stirring at room temperature for 0.5 h, the mixture was diluted with water (10 mL), extracted with ethyl acetate (3×5 mL), washed with brine (1×5 mL), dried (MgSO$_4$) and concentrated at reduced pressure. Purification by recrystallization with acetonitrile yielded Compound 7a (47 mg, 25% yield) and Compound 7b (30 mg, 16% yield) as white solids:

$^1$H NMR for Compound 7a (acetone-d$_6$, 300 MHz) δ 7.97 (d, J=8.1 Hz, 2H), 7.77 (d, J=16.5 Hz, 1H), 7.64 (d, J=8.1

Hz, 2H), 7.48 (d, J=1.8 Hz, 1H), 7.20 (dd, J=1.8, 8.1 Hz, 1H), 7.17–6.85 (m, 6H), 5.93 (t, J=4.5 Hz, 1H), 2.30 (d, J=5.1 Hz, 2H), 2.29 (s, 3H), 1.27 (s, 6H);

$^1$H NMR for Compound 7b (acetone-$d_6$, 300 MHz) δ 7.87 (d, J=8.4 Hz, 2H), 7.49 (d, J=8.4 Hz, 2H), 7.24 (d, J=1.5 Hz, 1H), 7.17–7.09 (m, 5H), 6.98 (dd, J=1.5, 6.9 Hz, 1H), 6.46 (d, J=16.2 Hz, 1H), 2.27 (d, J=4.5 Hz, 2H), 2.25 (s, 3H), 1.23 (s, 6H).

4-[3-(8,8-Dimethyl-5-p-tolyl-7,8-dihydro-naphthalen-2-yl)-3-hydroximino-propenyl]-benzoic Acid (Compound 7c)

To a solution of 2-trimethylsilanyl-ethyl 4-[3-(8,8-dimethyl-5-p-tolyl-7,8-dihydro-naphthalen-2-yl)-3-oxo-propenyl]-benzoate (Compound 6, 240 mg, 0.46 mmol) in 5 mL of EtOH was added hydroxylamine hydrochloride (64 mg, 0.92 mmol) and pyridine (77 mg, 0.97 mmol). The reaction mixture was then heated at reflux for 6 h. After cooling to room temperature, the solvent was removed in vacuo and the residue was taken up in water. The aqueous layer was adjusted to pH=4–5 with 1 N HCl and extracted with ethyl acetate (3×10 mL). The organic layers were combined and washed with water (2×10 mL) and brine (1×10 mL), dried (MgSO$_4$) and concentrated at reduced pressure to obtain a yellow crude oil. This crude product was then dissolved in 2 mL of dimethylsulfoxide (DMSO) and tetraethylammomium fluoride (TEAF) (137 g, 0.92 mmol) was added. After stirring at room temperature for 0.5 h, the mixture was diluted with water (10 mL), extracted with ethyl acetate (3×5 mL), washed with brine (1×5 mL), dried (MgSO$_4$) and concentrated at reduced pressure. Purification by recrystallization with acetonitrile yielded Substance 7c, (a mixture of E/Z isomers, 84 mg, 42% yield).

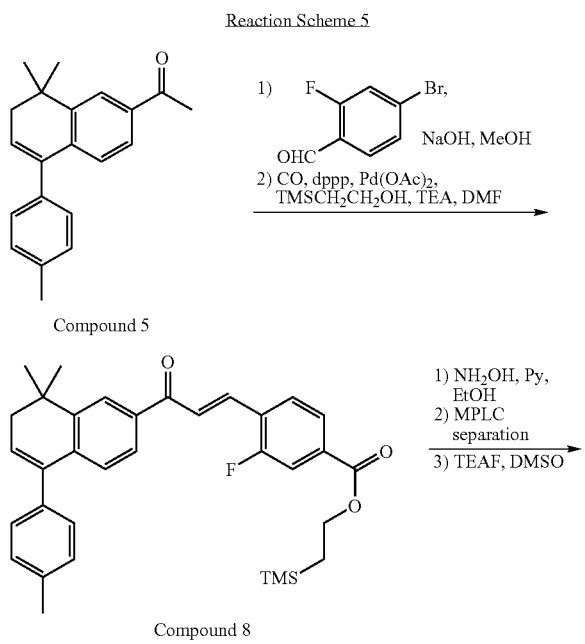

Reaction Scheme 5

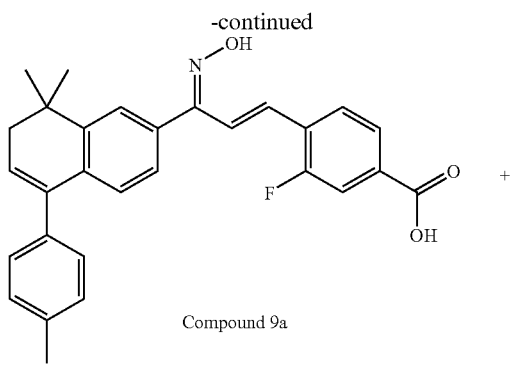

Compound 9a

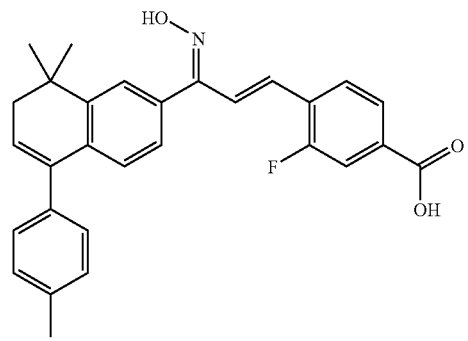

Compound 9b

2-Trimethylsilanyl-ethyl 4-[3-(8,8-dimethyl-5-p-tolyl-7,8-dihydro-naphthalen-2-yl)-3-oxo-propenyl]-3-fluoro-benzoate (Compound 8)

4-Bromo-2-fluoro-benzaldehyde (available from Aldrich, 151 mg, 0.75 mmol) was added to a solution of 1-(8,8-dimethyl-5-p-tolyl-7,8-dihydro-naphthalen-2-yl)-ethanone (Compound 5, 217 mg, 0.75 mmol) in 10 mL of 1 N NaOH and 20 mL of methanol. After stirring at room temperature for 18 h, the reaction mixture was extracted with ethyl acetate (3×10 mL). The combined organic layer was washed with brine (1×10 mL), dried (MgSO$_4$) and concentrated at reduced pressure to give a crude white solid. This solid was then transferred to a sealed tube containing 1,3-bis(diphenylphosphino)propane (33 mg, 0.08 mmol) and palladium acetate (18 mg, 0.08 mmol) in 20 mL dimethylformamide (DMF), 5 mL of triethylamine (TEA) and 2 mL of trimethylsilylethanol. After bubbling carbon monoxide into the solution for 20 min, the tube was sealed and heated at 85° C. for 48 h. The reaction mixture was then cooled to room temperature and the solvent was removed in vacuo. The residue was dissolved in 30 mL dichloromethane, washed with 1N HCl (2×20 mL) and brine (2×20 mL). The organic layer was then dried (MgSO$_4$) and concentrated at reduced pressure. Purification by flash chromatography (90:10 hexane/ethyl acetate) afforded the title compound (168 mg, 41% yield) as a colorless oil:

$^1$H NMR (CDCl$_3$, 300 MHz) δ 8.05 (d, J=1.5 Hz, 1H), 7.85–7.62 (m, 6H), 7.21 (s, 4H), 7.19 (d, J=8.1 Hz, 1H), 6.18

(t, J=4.8 Hz, 1H), 4.44–4.40 (m, 2H), 2.40 (s, 3H), 2.39 (d, J=4.5 Hz, 2H), 1.40 (s, 6H), 1.20–1.17 (m, 2H) 0.00 (s, 9H).

E-4-[3-(8,8-Dimethyl-5-p-tolyl-7,8-dihydro-naphthalen-2-yl)-3-hydroxyimino-propenyl]-3-fluoro-benzoic Acid (Compound 9a) and Z-4-[3-(8,8-Dimethyl-5-p-tolyl-7,8-dihydro-naphthalen-2-yl)-3-hydroxyimino-propenyl]-3-fluoro-benzoic Acid (Compound 9b)

Following Procedure A while using 2-trimethylsilanyl-ethyl 4-[3-(8,8-dimethyl-5-p-tolyl-7,8-dihydro-naphthalen-2-yl)-3-oxo-propenyl]-3-fluoro-benzoate (Compound 8, 168 mg, 0.31 mmol) as the starting material afforded Compound 9a (34 mg, 24% yield) and Compound 9b (20 mg, 14% yield) as white solids:

$^1$H NMR for Compound 9a (acetone-d$_6$, 300 MHz) δ 7.85–7.78 (m, 3H), 7.63 (dd, J=1.5, 11.4 Hz, 1H), 7.48 (d, J=1.8 Hz, 1H), 7.20 (dd, J=1.8, 8.1 Hz, 1H), 7.17 (s, 4H), 7.00–6.95 (m, 2H), 5.92 (t, J=4.8 Hz, 1H), 2.29 (d, J=4.8 Hz, 2H), 2.27 (s, 3H), 1.26 (s, 6H);

$^1$H NMR for Compound 9b (acetone-1,300 MHz) δ 7.89–7.84 (m, 2H), 7.68 (d, J=11.1 Hz, 1H), 7.39–7.07 (m, 9H), 6.70 (d, J=16.5 Hz, 1H), 2.38 (d, J=4.8 Hz, 2H), 2.37 (s, 3H), 1.36 (s, 6H).

Synthesis of Indene Exemplary Compounds of the Invention

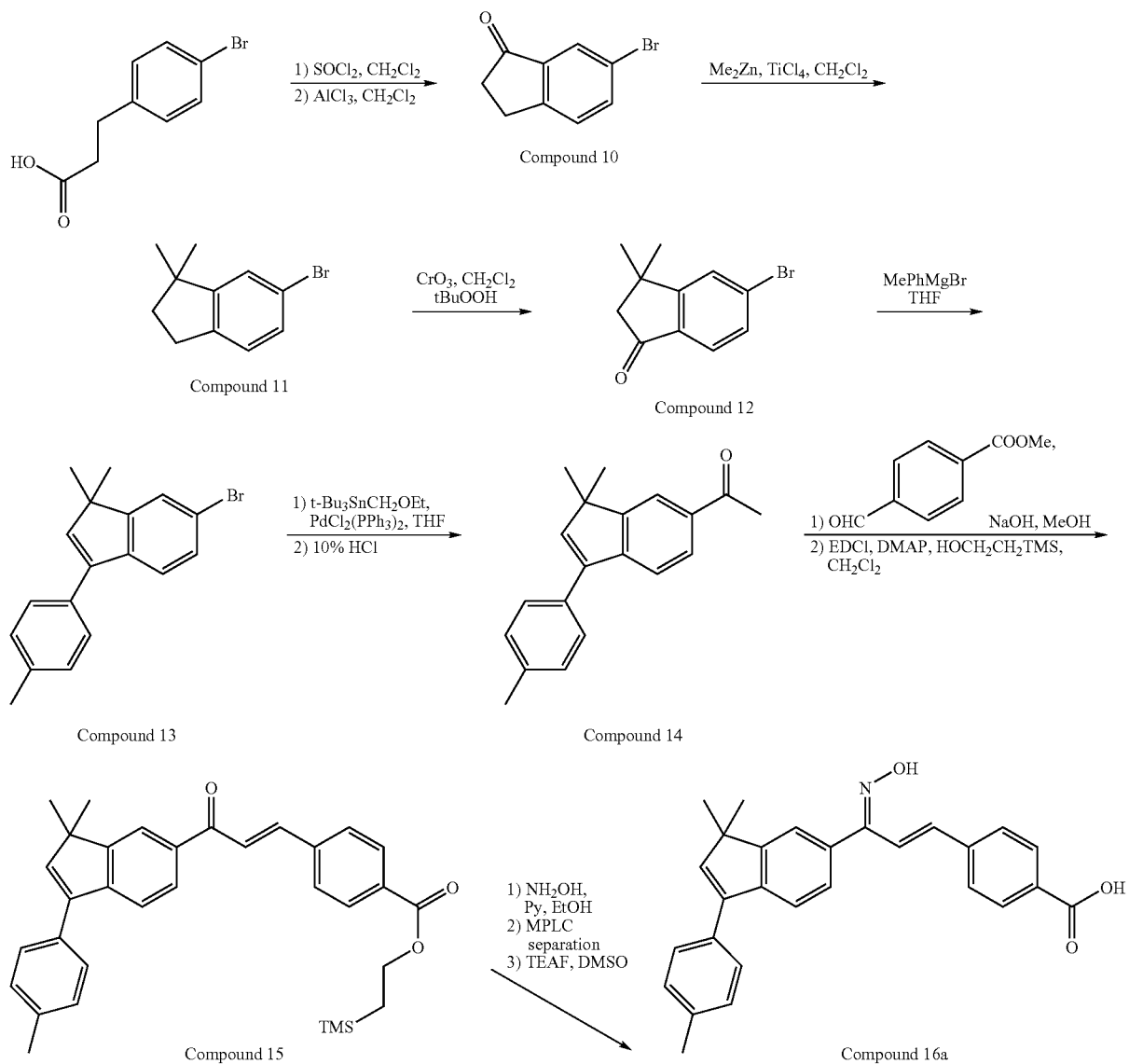

Reaction Scheme 6

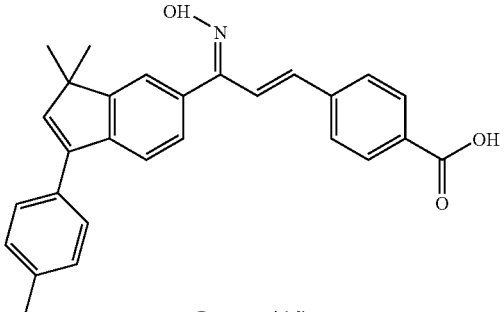

Compound 16b

6-Bromo-indan-1-one (Compound 10)

Thionyl chloride (15.6 g, 131.1 mmol) was added slowly to a solution of 3-(4-bromo-phenyl)-propionic acid (available from Transworld Chemicals, 10.0 g, 43.7 mmol) in 100 mL of dichloromethane at room temperature. The mixture was then heated at reflux for 14 h. After cooling to room temperature, the solvent and excess thionyl chloride were removed under reduced pressure to afford a yellow crude oil. The crude product was then dissolved in 100 mL of dichloromethane and aluminum chloride (17.5 g, 131.1 mmol) was added portionwise at room temperature. After heating at reflux for 5 h, the mixture was then slowly poured into ice-water, extracted with dichloromethane (3×50 mL), washed with brine (1×50 mL), dried ($MgSO_4$) and concentrated at reduced pressure. Purification by flash chromatography (95:5 hexane/ethyl acetate) yielded the title compound (8.94 g, 97% yield) as a light yellow solid:
$^1$H NMR ($CDCl_3$, 300 MHz) δ 7.88 (d, J=2.1 Hz, 1H), 7.68 (dd, J=2.1, 8.1 Hz, 1H), 7.36 (d, J=8.1 Hz, 1H), 3.12–3.08 (m, 2H), 2.75–2.71 (m, 2H).

6-Bromo-1,1-dimethyl-indan (Compound 11)

To a solution of 24.6 mL of 1 M titanium chloride (24.6 mmol) in 20 mL of dichloromethane at −40° C. was slowly added 17.6 mL of 2 M dimethyl zinc in toluene (35.1 mmol). After stirring at −40° C. for 20 min, the mixture was added a solution of 6-bromo-indan-1-one (Compound 10, 2.46 g, 11.7 mmol) in 20 mL of dichloromethane through cannulation. The reaction was then slowly warmed to room temperature for 18 h. After quenching with methanol at 0° C., the mixture was extracted with dichloromethane (3×10 mL). The combined organic layer was washed with brine (1×10 mL), dried ($MgSO_4$) and concentrated at reduced pressure. Purification by flash chormatography (hexane) yielded the title compound (2.45 g, 94% yield) as a colorless oil:
$^1$H NMR ($CDCl_3$, 300 MHz) δ 7.25–7.22 (m, 2H), 7.04 (d, J=8.1 Hz, 1H), 2.82 (t, J=6.9 Hz, 2H), 1.92 (t, J=6.9 Hz, 2H), 1.24 (s, 6H).

5-Bromo-3,3-dimethyl-indan-1-one (Compound 12)

Following a procedure similar to that for the preparation of 6-bromo-4,4-dimethyl-3,4-dihydro-2H-naphthalen-1-one (Compound 3) while using 6-bromo-1,1-dimethyl-indan (Compound 11, 2.45 g, 10.9 mmol) as the starting material afforded the title compound (1.95 g, 75% yield) as a white solid:
$^1$H NMR ($CDCl_3$, 300 MHz) δ 7.66 (d, J=1.5 Hz, 1H), 7.55 (d, J=8.4 Hz, 1H), 7.51 (dd, J=1.5, 8.4 Hz, 1H), 2.59 (s, 2H), 1.43 (s, 6H).

6-Bromo-1,1-dimethyl-3-p-tolyl-1H-indene (Compound 13)

Following a procedure similar to that for the preparation of 7-bromo-1,1-dimethyl-4-p-tolyl-1,2-dihydro-naphthalene (Compound 4) while using 5-bromo-3,3-dimethyl-indan-1-one (Compound 12, 1.00 g, 4.2 mmol) as the starting material yielded the title compound (981 mg, 75% yield) as a colorless oil:
$^1$H NMR ($CDCl_3$, 300 MHz) δ 7.49–7.23 (m, 7H), 6.35 (s, 1H), 2.40 (s, 3H), 1.38 (s, 6H).

1-(3,3-Dimethyl-1-p-tolyl-3H-inden-5-yl)-ethanone (Compound 14)

Following a procedure similar to that for the preparation of 1-(8,8-dimethyl-5-p-tolyl-7,8-dihydro-naphthalen-2-yl)-ethanone (Compound 5) while using 6-bromo-1,1-dimethyl-3-p-tolyl-1H-indene (Compound 13, 980 mg, 3.14 mmol) as the starting material afforded the title compound (678 mg, 78% yield) as a yellow solid:
$^1$H NMR ($CDCl_3$, 300 MHz) δ 7.99 (d, J=1.5 Hz, 1H), 7.89 (dd, J=1.5, 8.4 Hz, 1H), 7.54 (d, J=8.4 Hz, 1H), 7.47 (d, J=8.4 Hz, 2H), 7.27 (d, J=8.4 Hz, 2H), 6.57 (s, 1H), 2.64 (s, 3H), 2.42 (s, 3H), 1.42 (s, 6H).

2-Trimethylsilanyl-ethyl 4-[3-(3,3-dimethyl-1-p-tolyl-3H-inden-5-yl)-3-oxo-propenyl]-benzoate (Compound 15)

Following a procedure similar to that for the preparation of 2-trimethylsilanyl-ethyl 4-[3-(8,8-dimethyl-5-p-tolyl-7,8-dihydro-naphthalen-2-yl)-3-oxo-propenyl]-benzoate (Compound 6) while using 1-(3,3-dimethyl-1-p-tolyl-3H-inden-5-yl)-ethanone (Compound 14, 200 mg, 0.72 mmol) as the starting material yielded the title compound (93 mg, 25% yield) as a yellow solid:
$^1$H NMR ($CDCl_3$, 300 MHz) δ 8.05–8.01 (m, 4H), 7.93 (dd, J=1.8, 8.4 Hz, 1H), 7.77–7.43 (m, 5H), 7.24–7.20 (m, 3H), 6.54 (s, 1H), 4.43–4.37 (m, 2H), 2.37 (s, 3H), 1.41 (s, 6H), 1.13–1.11 (m, 2H), 0.00 (s, 9H).

E-4-[3-(3,3-Dimethyl-1-p-tolyl-3H-inden-5-yl)-3-hydroxyimino-propenyl]-3-fluoro-benzoic acid (Compound 16a) and Z-4-[3-(3,3-Dimethyl-1-p-tolyl-3H-inden-5-yl)-3-hydroxyimino-propenyl]-3-fluoro-benzoic acid (Compound 16b)

Following Procedure A while using 2-trimethyl-silanyl-ethyl 4-[3-(3,3-dimethyl-1-p-tolyl-3H-inden-5-yl)-3-oxo-propenyl]-benzoate (Compound 15, 93 mg, 0.18 mmol) as the starting material afforded Compound 16a (19 mg, 26% yield) and Compound 16b (12 mg, 16% yield) as white solids:

$^1$H NMR for Compound 16a (acetone-1,300 MHz) δ 8.05 (d, J=8.4 Hz, 2H), 7.89 (d, J=16.5 Hz, 1H), 7.72 (d, J=8.4 Hz, 2H), 7.63 (d, J=1.5 Hz, 1H), 7.56–7.46 (m, 4H), 7.30 (d, J=8.4 Hz, 2H), 6.95 (d, J=16.5 Hz, 1H), 6.56 (s, 1H), 2.38 (s, 3H), 1.42 (s, 6H);

$^1$H NMR for Compound 16b (acetone-d$_6$, 300 MHz) δ 8.02 (d, J=8.4 Hz, 2H), 7.62–7.54 (m, 5H), 7.46–7.24 (m, 5H), 6.60 (d, J=16.5 Hz, 1H), 6.56 (s, 1H), 2.39 (s, 3H), 1.43 (s, 6H).

Reaction Scheme 7

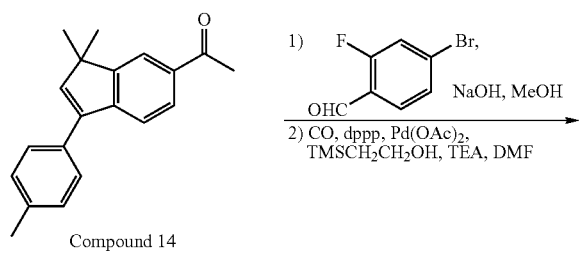

Compound 14

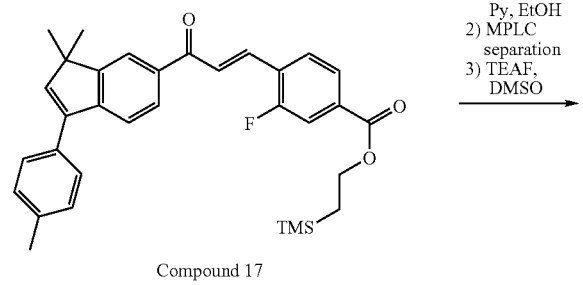

Compound 17

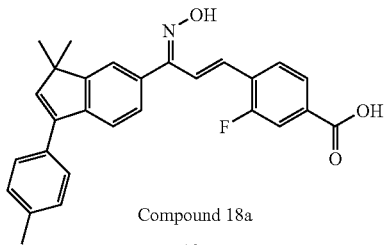

Compound 18a

+

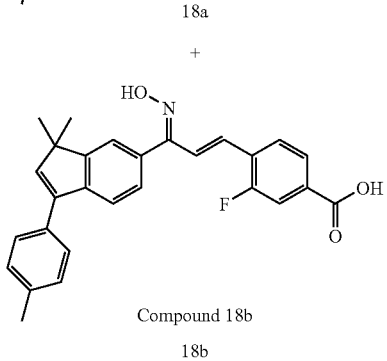

Compound 18b

2-Trimethylsilanyl-ethyl 4-[3-(3,3-dimethyl-1-p-tolyl-3H-inden-5-yl)-3-oxo-propenyl]-3-fluoro-benzoate (Compound 17)

Following a procedure similar to that for the preparation of 2-trimethylsilanyl-ethyl 4-[3-(8,8-dimethyl-5-p-tolyl-7,8-dihydro-naphthalen-2-yl)-3-oxo-propenyl]-3-fluoro-benzoate (Compound 8) while using 1-(3,3-dimethyl-1-p-tolyl-3H-inden-5-yl)-ethanone (Compound 14, 200 mg, 0.72 mmol) as the starting material yielded the title compound (145 mg, 38% yield) as a yellow solid:

$^1$H NMR (CDCl$_3$, 300 MHz) δ 8.01 (d, J=1.5 Hz, 1H), 7.95–7.68 (m, 5H), 7.54 (d, J=8.1 Hz, 1H), 7.45–7.42 (m, 3H), 7.21 (d, J=8.1 Hz, 2H), 6.54 (s, 1H), 4.42–4.36 (m, 2H), 2.36 (s, 3H), 1.40 (s, 6H), 1.13–1.07 (m, 2H), 0.00 (s, 9H).

E-4-[3-(3,3-Dimethyl-1-p-tolyl-3H-inden-5-yl)-3-hydroxyimino-propenyl]-3-fluoro-benzoic acid (Compound 18a) and Z-4-[3-(3,3-Dimethyl-1-p-tolyl-3H-inden-5-yl)-3-hydroxyimino-propenyl]-3-fluoro-benzoic acid (Compound 18b)

Following Procedure A while using 2-trimethyl-silanyl-ethyl 4-[3-(3,3-dimethyl-1-p-tolyl-3H-inden-5-yl)-3-oxo-propenyl]-3-fluoro-benzoate (Compound 17, 145 mg, 0.28 mmol) as the starting material yielded Compound 18a (39 mg, 32% yield) and Compound 18b (14 mg, 12% yield) as white solids:

$^1$H NMR for Compound 18a (acetone-d$_6$, 300 MHz) δ 7.99–7.88 (m, 3H), 7.74–7.45 (m, 6H), 7.30 (d, J=8.1 Hz, 2H), 7.06 (d, J=17.1 Hz, 1H), 6.56 (s, 1H), 2.38 (s, 3H), 1.42 (s, 6H);

$^1$H NMR for Compound 18b (acetone-d$_6$, 300 MHz) δ 7.87–7.85 (m, 3H), 7.70–7.29 (m, 8H), 6.73 (d, J=16.5 Hz, 1H), 6.57 (s, 1H), 2.40 (s, 3H), 1.44 (s, 6H).

Synthesis of Thiochromene Exemplary Compounds of the Invention
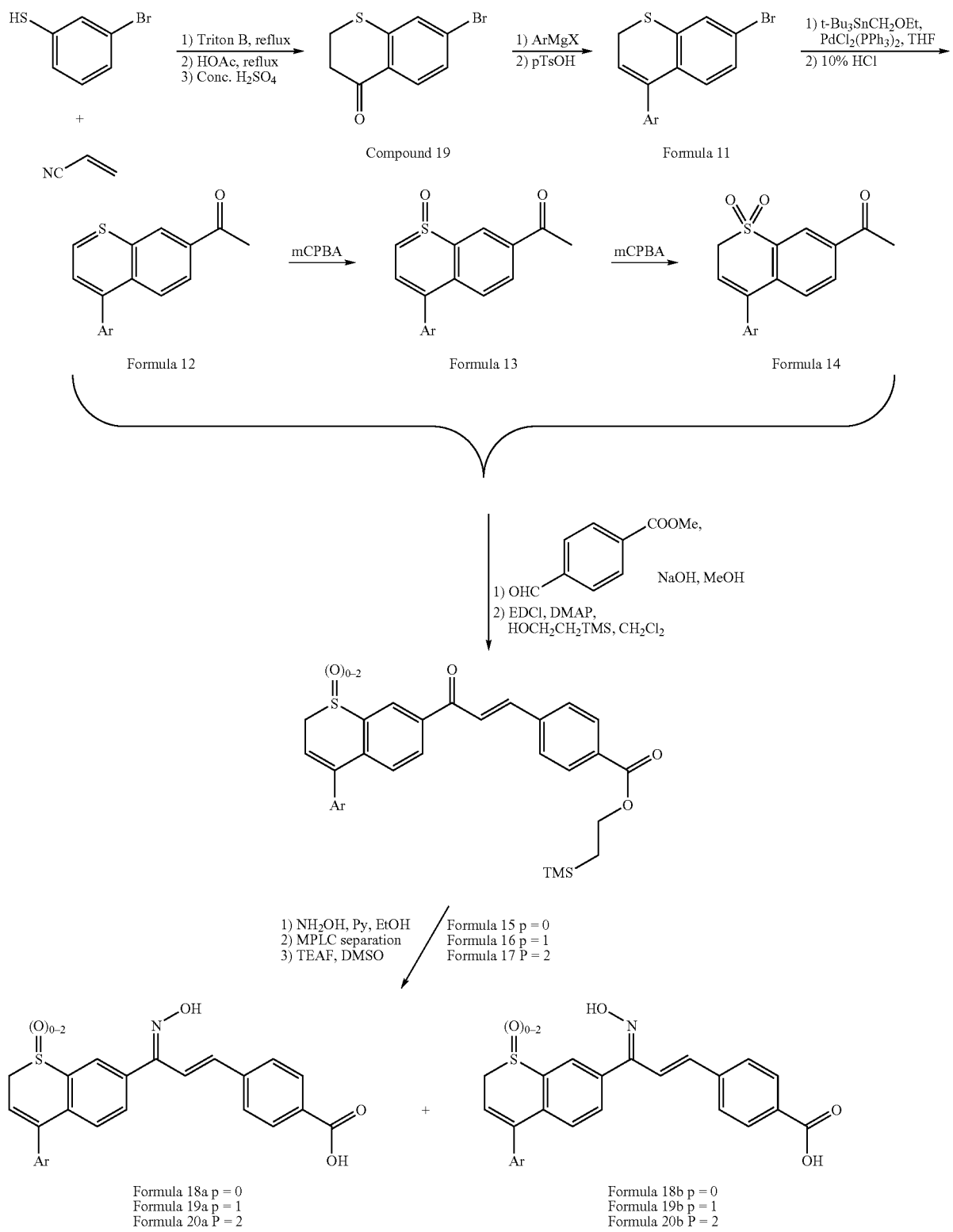

Reaction Scheme 8 provides examples for preparing compounds of the invention which are thiochromene derivatives, that is where the variable R of Formula 1 is represented by Formula (d). For the sake of simplicity of illustration the scheme illustrates the synthesis of the compounds of the invention where the variable Y represents a phenyl group and where X represents an aryl group Ar (for example a phenyl or tolyl group) substituting carbon 4 of the non-aromatic portion of the thiochromene nucleus.

Thus, in accordance with Reaction Scheme 8, 5-bromothiophenol (available from Aldrich) is reacted with the reagent Triton B (benzyltrimethylammonium hydroxide, available from Alrich), thereafter refluxed with acidic acid, and thereafter treated with concentrated sulfuric acid to yield 7-bromo-thiochroman-4-one (Compound 19). Thereafter Compound 19 is reacted with a Grignard reagent of the formula ArMgX where Ar represents an aryl or heteroaryl group of the type that fits within the definition of the variable X in connection with Formula 1. Phenylmagnesium chloride and para-tolylmagnesium chloride serve as examples for the Grignard reagent ArMgX. The reaction of Compound 19 with the Grignard reagent gives rise to a tertiary alcohol (not shown in the scheme) that is reacted with acid (for example with para-toluenesulfonic acid, TsOH) to provide a 4-aryl-7-bromo-thiochromene compound of Formula 11. The compound of Formula 11 is then reacted in vinyl-nitrile with tributyl(1-ethoxyvinyl)tin in the presence of a palladium catalyst ($PdCl_2(PPh_3)_2$), and thereafter with acid to provide the methyl ketone of Formula 12. The compound of Formula 12 can be oxidized with a suitable reagent, such as meta-chloroperbenzoic acid, to the sulfoxide and to the sulfone level to yield the compounds of Formula 13 and 14, respectively. Each of the methyl ketones having the Formulas 12, 13 and 14 can be made to undergo aldol condensation with a reagent of Formula 3 (as shown in Reaction Scheme 1. However, in this reaction scheme for the sake of simplicity the reaction of the compounds of Formulas 12, 13 and 14 with methyl 4-formylbenzoate is shown, because methyl 4-formylbenzoate is a preferred example of the reagents of Formula 3. The aldol condensation with methyl 4-formylbenzoate is followed by esterification of the resulting intermediate products to provide the chalcone compounds of Formulas 15, 16 and 17, respectively. These are converted into the chalcone oxime compounds with hydroxylamine and de-esterified by treatment with tetraethylammomium fluoride (TEAF) to give the chalcone oxime compounds of the invention, having the Formulas 18a, 18b, 19a, 19b, 20a and 20b, respectively.

Synthesis of Dihydroquinoline Exemplary Compounds of the Invention

Reaction Scheme 9

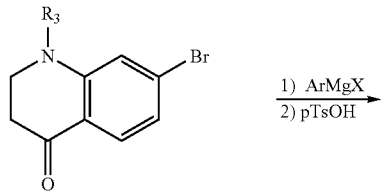

Formula 21

European Patent EP0243982

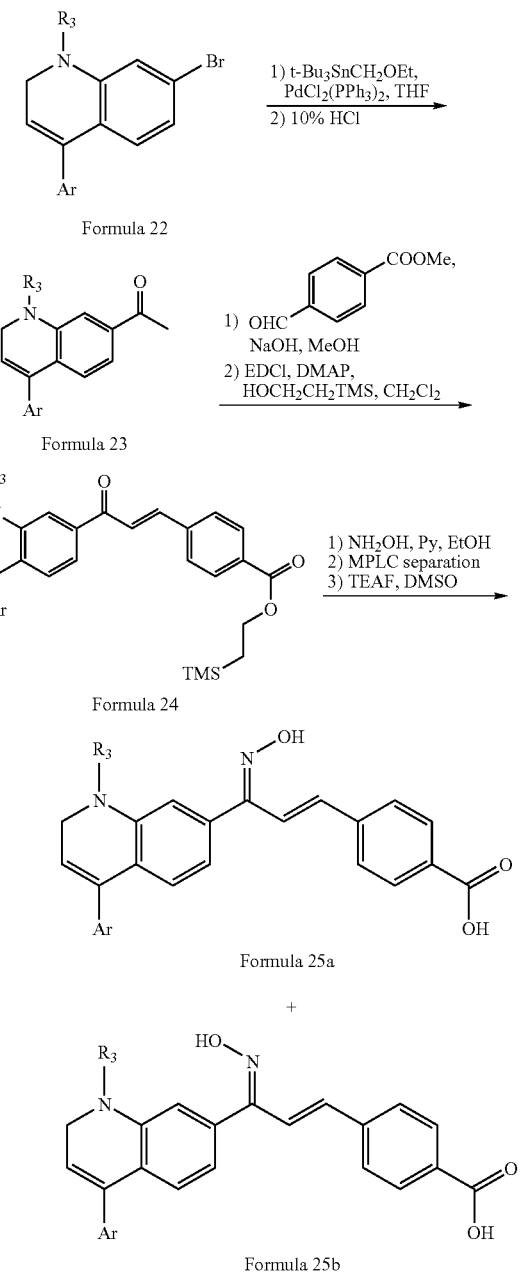

The starting compound for the synthesis of dihydroquinoline derivatives of the present invention is an N-alkyl-7-bromo-1,2-dihydroquinolin-4-one compound of Formula 21, wherein the $R_3$ group is defined as in connection with Formula 1. The compounds of Formula 21 can be obtained in accordance with the disclosure of European Patent No. EP 024 982 which is expressly incorporated herein by reference. In accordance with Reaction Scheme 9 the compounds of Formula 21 are reacted with a Grignard reagent of the formula ArMgX where Ar is defined as in connection with Reaction Scheme 8. The remaining reactions which lead to compounds of the invention shown in Formulas 25a and 25b are analogous to the reaction described in connection with Reaction Scheme 8, and need not be repeated here.

What is claimed is:

1. A compound of the formula

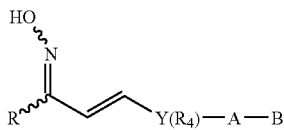

wherein R is selected from the groups consisting of the radicals defined by formulas (a) through (d)

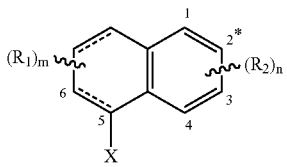 Formula (a)

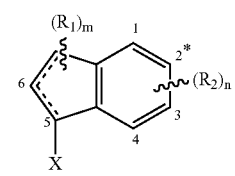 Formula (b)

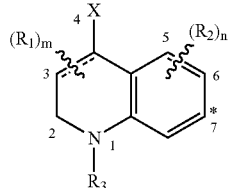 Formula (c)

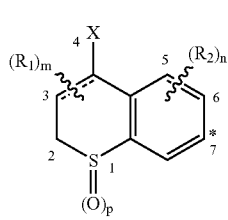 Formula (d)

where the dashed line in a ring represents a bond, or absence of a bond with the proviso that one and only one dashed line in the ring represents a bond;

a * denotes a ring carbon to which the chalcone oxime group is attached;

X is $(R_5)_r$-substituted alkenyl of 1–6 carbons and 1 or 2 double bonds, $(R_5)_r$-substituted alkynyl of 1–6 carbons and 1 or 2 triple bonds, $(R_5)_r$-phenyl, $(R_5)_r$-naphthyl, $(R_5)_r$-heteroaryl where the heteroaryl group has 1 to 3 heteroatoms selected from the group consisting of O, S and N;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_4$ groups;

m is an integer having the values 0 to 5;
n is an integer having the values 0 to 3;
p is an integer having the values 0 to 2;
r is an integer having the values 0 to 5;

$R_1$ is independently alkyl of 1 to 6 carbons, F, Cl, Br or I;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl) amino;

$R_3$ is H or alkyl of 1 to 10 carbons;

$R_4$ is independently halogen, alkyl of 1 to 10 carbons, fluoro substituted alkyl of 1 to 6 carbons, alkoxy of 1 to 10 carbons, or alkylthio of 1 to 10 carbons;

$R_5$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl) amino;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

2. A compound in accordance with claim 1 wherein Y is selected from the groups consisting of pheny, pyridyl, thienyl and furyl.

3. A compound in accordance with claim 2 where Y is phenyl.

4. A compound in accordance with claim 3 where the Y group is substituted by the chalcone-oxime and the A-B group in 1,4 (para) positions.

5. A compound in accordance with claim 1 where the R group is represented by formula (a).

6. A compound in accordance with claim 5 where the dashed line between carbons 5 and 6 represents a bond.

7. A compound in accordance with claim 6 where X is $(R_5)_r$-phenyl.

8. A compound in accordance with claim 7 where $(R_5)_r$ is methyl.

9. A compound in accordance with claim 1 where the R group is represented by formula (b).

10. A compound in accordance with claim 9 where the dashed line between carbons 5 and 6 represents a bond.

11. A compound in accordance with claim 10 where X is $(R_5)_r$-phenyl.

12. A compound in accordance with claim 11 where $(R_5)_r$ is methyl.

13. A compound of the formula

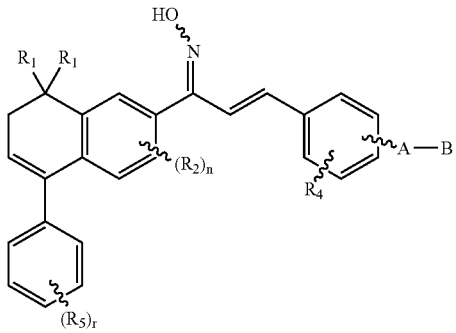

wherein $R_1$ is alkyl of 1 to 6 carbons;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_4$ is independently halogen, alkyl of 1 to 10 carbons, fluoro substituted alkyl of 1 to 6 carbons, alkoxy of 1 to 10 carbons, or alkylthio of 1 to 10 carbons;

$R_5$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

n is an integer having the values 0 to 3;

r is an integer having the values 0 to 5;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

14. A Compound in accordance with claim 13 that has the formula

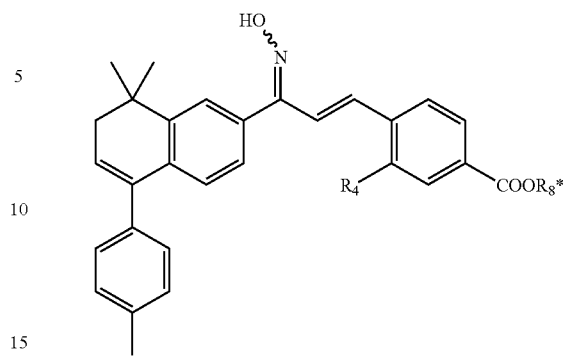

where $R_4$ is H or F, and $R_8$* is H, alkyl of 1 to 6 carbons, $CH_2OCH_3$ or $CH_2OCH_2OOC_{1-6}$alkyl, or a pharmaceutically acceptable salt of said compound.

15. A compound in accordance with claim 14 where $R_8$* is H, or a pharmaceutically acceptable salt of said compound.

16. A compound of the formula

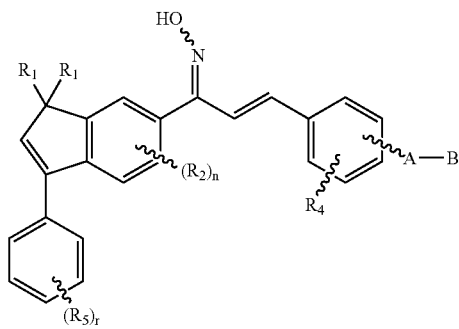

wherein $R_1$ is alkyl of 1 to 6 carbons;

$R_2$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

$R_4$ is independently halogen, alkyl of 1 to 10 carbons, fluoro substituted alkyl of 1 to 6 carbons, alkoxy of 1 to 10 carbons, or alkylthio of 1 to 10 carbons;

$R_5$ is independently alkyl of 1 to 6 carbons, F, Cl, Br, I, OH, SH, alkoxy having 1 to 6 carbons, alkylthio having 1 to 6 carbons, $NH_2$, $C_{1-6}$alkylamino or di($C_{1-6}$alkyl)amino;

n is an integer having the values 0 to 3;

r is an integer having the values 0 to 5;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl group of 1 to 6 carbons, cycloalkyl of 3 to 5 carbons, or alkenyl group containing 2 to 5 carbons, $R_8$ is an alkyl group of 1 to 10 carbons or trimethylsilylalkyl where the alkyl group has 1 to 10 carbons, or a cycloalkyl group of 5 to 10 carbons, $CH_2OCH_3$ or $CH_2OCH_2OOC_{1-6}$alkyl, or $R_8$ is phenyl or $C_{1-6}$ alkylphenyl, $R_9$ and $R_{10}$ independently are hydrogen, an alkyl group of 1 to 10 carbons, or a cycloalkyl group of 5–10 carbons, or phenyl or $C_{1-6}$alkylphenyl, $R_{11}$ is alkyl of 1 to 6 carbons, phenyl or $C_{1-6}$alkylphenyl, $R_{12}$ is alkyl of 1 to 6 carbons, and $R_{13}$ is divalent alkyl radical of 2–5 carbons, or a pharmaceutically acceptable salt of said compound.

17. A Compound in accordance with claim 16 that has the formula

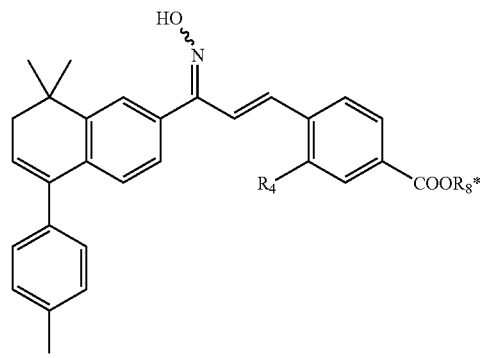

where $R_4$ is H or F, and $R_8$ is H, alkyl of 1 to 6 carbons, $CH_2OCH_3$ or $CH_2OCH_2OOC_{1-6}$alkyl, or a pharmaceutically acceptable salt of said compound.

18. A compound in accordance with claim 17 where $R_8$* is H, or a pharmaceutically acceptable salt of said compound.

* * * * *

UNITED STATES PATENT AND TRADEMARK OFFICE
CERTIFICATE OF CORRECTION

PATENT NO. : 7,253,319 B2
APPLICATION NO. : 11/021471
DATED : August 7, 2007
INVENTOR(S) : Kwok Yin Tsang et al.

It is certified that error appears in the above-identified patent and that said Letters Patent is hereby corrected as shown below:

Column 38
Line 17, delete "$R_8$" and insert therefor --$R_8^*$--

Signed and Sealed this

Second Day of June, 2009

JOHN DOLL
*Acting Director of the United States Patent and Trademark Office*

Disclaimer

7,253,319—Kwok Yin Tsang, Irvine, CA (US); Santosh Sinha, Irvine CA (US); Xiaoxia Liu, Tustin, CA (US); Smita Bhat, Irvine, CA (US); Roshantha A. Chandraratna, Laguna Hills, CA (US). DISUBSTITUTED CHALCONE OXIMES HAVING RARY RETINOID RECEPTOR ANTAGONIST ACTIVITY. Patent dated August 7, 2007. Disclaimer filed August 8, 2011, by the assignee, Allergan, Inc., Irvine, CA (US).

Hereby disclaims all of the claims 1-18 of said patent.

*(Official Gazette November 22, 2011)*